(12) United States Patent
Takahashi (10) Patent No.: US 11,426,299 B2
(45) Date of Patent: Aug. 30, 2022

(54) JOINT SUPPORT UNIT AND WALKING SUPPORT APPARATUS

(71) Applicant: SUNCALL CORPORATION, Kyoto (JP)

(72) Inventor: Rei Takahashi, Kyoto (JP)

(73) Assignee: SUNCALL CORPORATION, Kyoto (JP)

( * ) Notice: Subject to any disclaimer, the term of this patent is extended or adjusted under 35 U.S.C. 154(b) by 143 days.

(21) Appl. No.: 16/961,716

(22) PCT Filed: Dec. 27, 2018

(86) PCT No.: PCT/JP2018/048078
§ 371 (c)(1),
(2) Date: Jul. 13, 2020

(87) PCT Pub. No.: WO2019/138901
PCT Pub. Date: Jul. 18, 2019

(65) Prior Publication Data
US 2021/0052408 A1    Feb. 25, 2021

(30) Foreign Application Priority Data
Jan. 15, 2018    (JP) .............................. JP2018-004164

(51) Int. Cl.
*A61F 5/01*    (2006.01)
*A61H 1/02*    (2006.01)
*A61H 3/00*    (2006.01)

(52) U.S. Cl.
CPC .... *A61F 5/0123* (2013.01); *A61F 2005/0137* (2013.01); *A61H 1/0255* (2013.01);
(Continued)

(58) Field of Classification Search
CPC .. A61H 3/00; A61H 1/024; A61H 2201/1207; A61H 2201/1246;
(Continued)

(56) References Cited

U.S. PATENT DOCUMENTS 4,982,732 A * 1/1991 Morris ................. A61F 5/0125
403/96
5,938,629 A    8/1999 Bloedau

FOREIGN PATENT DOCUMENTS

| EP | 1579829 A1 | 9/2005 |
| GB | 2326098 A | 12/1998 |
| JP | 4092322 B2 | 5/2008 |

OTHER PUBLICATIONS

Extended European Search Report and Search Opinion dated Oct. 7, 2021 for corresponding European Patent Application No. EP18900358.5-122 / 3741346, 10 pages.

* cited by examiner

*Primary Examiner* — Ophelia A Hawthorne
(74) *Attorney, Agent, or Firm* — Locke Lord LLP (57) ABSTRACT

To provide a joint support unit, etc. capable of being worn on both left and right joints. A joint support unit includes a first link worn on one end side of a joint portion, a second link worn on the other end side of the joint portion, and rotatably coupled to the first link, a driving unit configured to perform rotation driving of the second link, and a rotation regulating unit configured to regulate a rotation direction and a rotation range of the second link. The rotation regulating unit includes an engagement body provided in one of the links, and an engagement part provided in the other one of the links, and engaging with the engagement body, the engagement part includes two guiding paths and that guide (Continued)

the engagement body moving according to the rotation direction of the second link in different directions, and a communication path.

9 Claims, 7 Drawing Sheets

(52) U.S. Cl.
CPC .... *A61H 2003/007* (2013.01); *A61H 2201/14* (2013.01); *A61H 2201/1676* (2013.01)

(58) Field of Classification Search
CPC ...... A61H 2201/164; A61H 2201/1642; A61H 2201/165; A61H 2201/1652; A61H 2201/1676; A61F 5/0111; A61F 5/0585; A61F 5/0195; A61F 5/0127
See application file for complete search history.

JOINT SUPPORT UNIT AND WALKING SUPPORT APPARATUS

TECHNICAL FIELD

The present invention relates to a joint support unit, etc. for supporting the movement of a joint of a user.

BACKGROUND ART

Walking support apparatuses used for supporting walking exercise, bending and stretching motion, rehabilitation, etc. of a patient with knee osteoarthritis have been conventionally known. There are a plurality of walking support apparatuses of this kind (for example, see Patent Literature 1), for example, the walking support apparatus illustrated in Patent Literature 1 is provided with a joint support unit that is worn on a knee joint of a user, and that includes a leg link for oscillating around the knee joint and its vicinity in the front and back directions by using an actuator.

The leg link includes a pair of links capable of being bent and stretched by rotation driving, is equipped with a driving source for driving a rotation axis of the links, and supports footsteps of the user with rotation driving of the links by the driving source.

CITATION LIST

Patent Literature

Patent Literature 1: Japanese Patent No. 4092322

SUMMARY OF INVENTION

Technical Problem

Since the driving directions are different when leg links are worn on left and right legs, it is necessary to separately manufacture exclusive apparatuses for left and right legs, which has been a factor for increasing the cost.

Also, generally, a walking support apparatus is manufactured and sold as a pair of left and right walking support units, and it has been necessary for a purchaser to purchase both left and right walking support units, even if only one side of the walking support units is required.

On the other hand, when a joint support unit provided in a walking support unit can be used for both left and right, the joint support unit is versatile and can easily reduce the cost.

Therefore, the present invention has been made while taking the above-described issue as an example of the problem, and aims at providing a joint support unit, etc. capable of being worn on both left and right joints.

Solution to Problem

In order to solve the above-described problem, the present invention adopts the following configurations. Note that in order to facilitate understanding of the present invention, the reference numerals in the drawings are written with parentheses in the description, but the present invention is not limited to this.

Specifically, a joint support unit (20) according to claim 1 is a joint support unit worn around a joint portion of a user, the joint support unit including a first link (21) worn on one end side of the joint portion, a second link (22) worn on the other end side of the joint portion, and rotatably coupled to the first link, a driving unit configured to perform rotation driving of the second link, and a rotation regulating unit (30) configured to regulate a rotation direction and a rotation range of the second link, the rotation regulating unit including an engagement body provided in one of the links, and an engagement part (33) provided in the other one of the links, and engaging with the engagement body, the engagement part including two guiding paths (34, 35) that guide the engagement body moving according to the rotation direction of the second link in different directions, and a communication path (39) that communicates the two guiding paths to each other, and the engagement body being movable between the two guiding paths via the communication path.

Additionally, the joint support unit according to claim 2 is characterized in that, in the joint support unit according to claim 1, each of the guiding paths includes a regulating portion (36a, 36b) configured to regulate a moving range of the engagement body.

Additionally, the joint support unit according to claim 3 is characterized in that the joint support unit according to claim 1 or claim 2 includes a moving unit (40) configured to move the engagement body to one or the other of the guiding paths.

Additionally, the joint support unit according to claim 4 is characterized in that the joint support unit according to any one of claims 1 to 3 includes a switching device configured to mechanically switch a rotation direction of the driving unit, when the engagement body is moved from one of the guiding paths to the other of the guiding paths.

Additionally, a walking support apparatus (S) according to claim 5 includes an upper leg wearing unit (5) worn from a knee joint of a leg to an upper leg portion (16), a lower leg wearing unit (10) worn from the knee joint to a lower leg portion (17), and a joint support unit (20) worn on the knee joint, the joint support unit including a first link coupled to the upper leg wearing unit, a second link coupled to the lower leg wearing unit, and rotatably coupled to the first link, a driving unit configured to rotate the second link, and a rotation regulating unit configured to regulate a rotation direction and a rotation range of the second link, the rotation regulating unit including an engagement body provided in one of the links, and an engagement part provided in the other one of the links, and engaging with the engagement body, the engagement part including two guiding paths that guide the engagement body moving according to the rotation direction of the second link in different directions, and a communication path that communicates the two guiding paths to each other, and the engagement body being movable between the two guiding paths via the communication path.

Advantageous Effects of Invention

Since the joint support unit can be worn on both left and right legs merely by inverting the joint support unit, the cost can be reduced. Additionally, since it does not operate beyond the range of movement of a knee joint specified in advance, it can be used safely. Further, since it is possible to simultaneously perform the mechanical switching operation of the joint support unit and the switching operation of an electrical control program of a power source (a motor, etc.), it is excellent in operativity and safety.

BRIEF DESCRIPTION OF DRAWINGS

FIG. 1 is a schematic diagram showing usage sates of a walking support apparatus.

FIG. 5 is a schematic diagram for describing the configuration of the moving unit.

FIG. 6 is a schematic diagram showing an operation example of the joint support unit worn on a left leg.

FIG. 7 is a schematic diagram showing an operation example of the joint support unit worn on a right leg.

DESCRIPTION OF EMBODIMENT

Hereinafter, an embodiment of the present invention will be described with reference to the drawings. Note that, in the following description, a description will be given of a walking support apparatus in which a joint support unit is used for a knee joint of a user. Additionally, in the following description, a "bending motion" refers to a motion of bending a knee joint, and a "stretching motion" refers to a motion of stretching the knee joint.

As shown in FIG. 1, a walking support apparatus S of the present embodiment is worn on a leg of the user, and includes a walking support unit U capable of being worn on both left and right legs. This walking support unit U includes an upper leg wearing unit 5 worn from a knee joint to an upper leg portion 16 of a leg, a lower leg wearing unit 10 worn from the knee joint to a lower leg portion 17, and a joint support unit 20 worn on the knee joint. Note that the walking support apparatus S is used by being coupled to, for example, a waist wearing unit 2 worn around the waist of the user, and in a case where support for both legs are required, the walking support unit U is worn on each of the left and right legs.

Figure 1A:
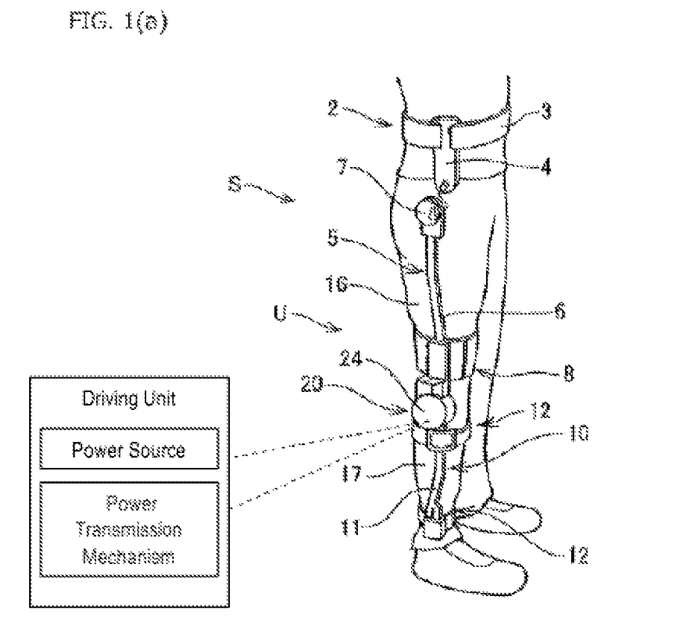
FIG. 1(a) shows a state where a leg is stretched.
Figure 1B:
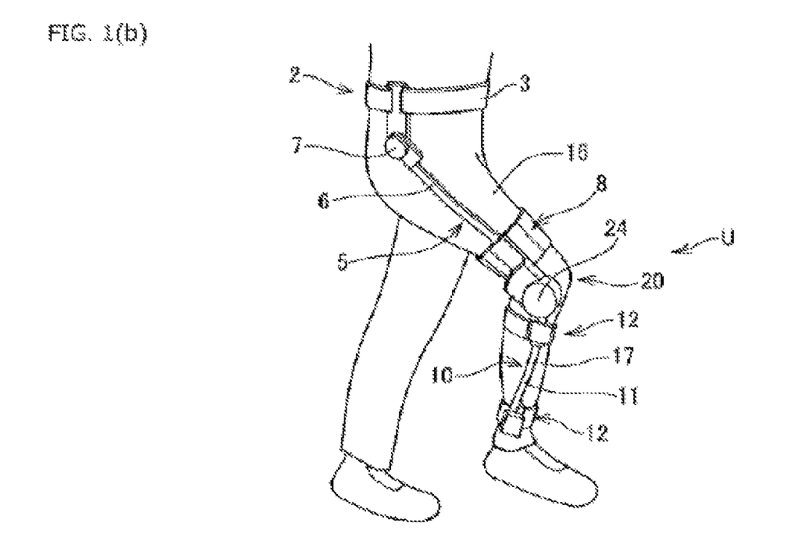
FIG. 1(b) shows a state where the leg is bent.

This walking support unit U performs walking support by causing the user to appropriately perform, for example, a stretching motion shown in FIG. 1(a), and a bending motion shown in FIG. 1(b), by oscillating the lower leg wearing unit 10 in the front and back directions with respect to the upper leg wearing unit 5 by driving, for example, a motor as a power source.

The waist wearing unit 2 includes a waist belt 3 wound around and attached to the waist of the user, and a coupling tool 4 coupled to the upper leg wearing unit 5 is provided on the left and right of the waist belt 3.

The upper leg wearing unit 5 includes a plate-like upper leg portion plate 6 arranged on a side surface of the upper leg portion 16 of the user, a top end thereof is rotatably coupled to the waist wearing unit 2 via a coupling tool 7, and the upper leg portion plate 6 is attached to rise along a lateral surface of the upper leg portion 16. Additionally, the upper leg portion plate 6 is provided with a contact member to be contacted to a part of the upper leg portion 16, and an attaching tool 8, such as a hook and loop fastener, for causing the contact member to stick to the upper leg portion 16, and the upper leg portion plate 6 is fixed and attached above a knee by this attaching tool 8.

Additionally, the lower leg wearing unit 10 includes a plate-like lower leg portion plate 11 arranged on a side surface of the lower leg portion 17 of the user, a top end thereof is coupled to the upper leg portion plate 6 via the joint support unit 20, and the lower leg portion plate 11 is attached to hang down along a lateral surface of the lower leg portion 17. Further, the lower leg portion plate 11 is provided with a contact member to be contacted to a below knee portion and to an ankle, and an attaching tools 12, such as a hook and loop fastener, for causing the contact member to stick to the below knee portion and the ankle, and a bottom end of the lower leg portion plate 11 is fixed and attached to lateral surfaces of the below knee portion and the ankle by this attaching tool 12.

Figure 2:
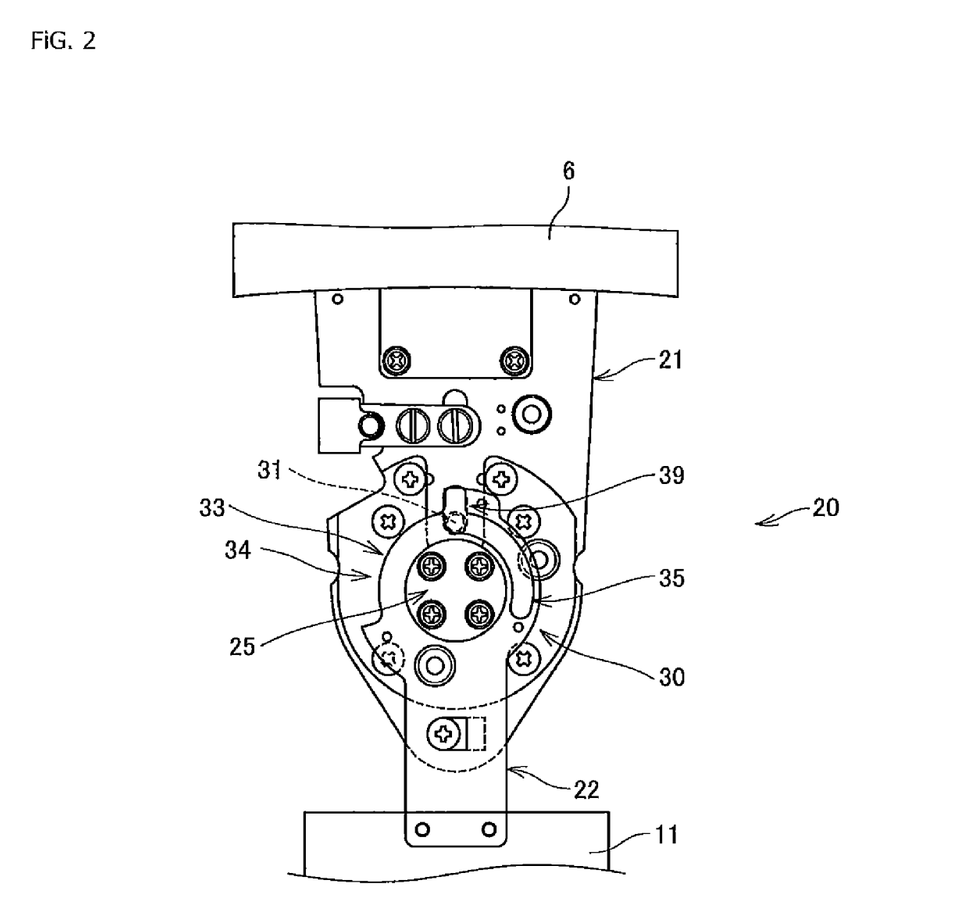
FIG. 2 is a schematic diagram showing the configuration of a joint support unit of the walking support apparatus.

As shown in FIG. 1 and FIG. 2, the joint support unit 20 includes a plate-like first link 21 that is arranged on the lateral surface of the knee joint of the user, and that is coupled to the upper leg portion plate 6, a plate-like second link 22 that is coupled to this first link 21 so as to be capable of being bent and stretched, and that is attached to the lower leg portion plate 11, a driving unit that is not shown and that causes the second link 22 to perform rotational movement in the front and back directions with respect to the first link 21, and a rotation regulating unit 30 that regulates the rotation direction and the rotation range of the second link 22.

Figure 3:
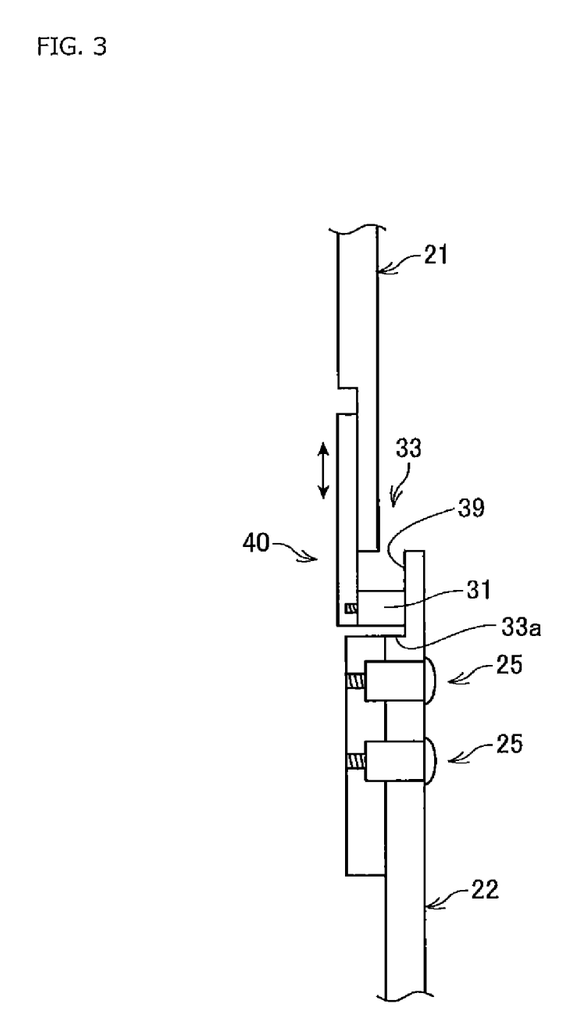
FIG. 3 is a schematic diagram showing a cross section for describing an operation example of a moving unit.

As shown in FIG. 3, the first link 21 and the second link 22 are, for example, superimposed on each other such that the second link 22 is arranged closer to the user to be rotatably coupled to each other by using four pin-like fixing screws 25, and the second link 22 is made to perform rotational movement by driving of the driving unit that is not shown and that is arranged on the outer side of the first link 21.

Although not shown, the driving unit includes a motor as a power source, a power transmission mechanism that transmits the torque of the motor to the second link 22, a control board that drives and controls the motor, a battery that supplies power supply to the motor, etc., and is, for example, loaded on the first link 21 and is received in a housing 24.

As shown in FIG. 2 and FIG. 3, the rotation regulating unit 30 includes a pin-like projection 31 (an example of an engagement body of the present application), and an engagement part 33 that engages with this projection 31. As shown in FIG. 3, the projection 31 is provided in the first link 21, and is provided to project toward the second link 22 side.

The engagement part 33 is formed in the second link 22, and includes two guiding paths 34 and 35 that guide the projection 31 according to the rotation operations in two different directions of the second link 22.

Figure 4:
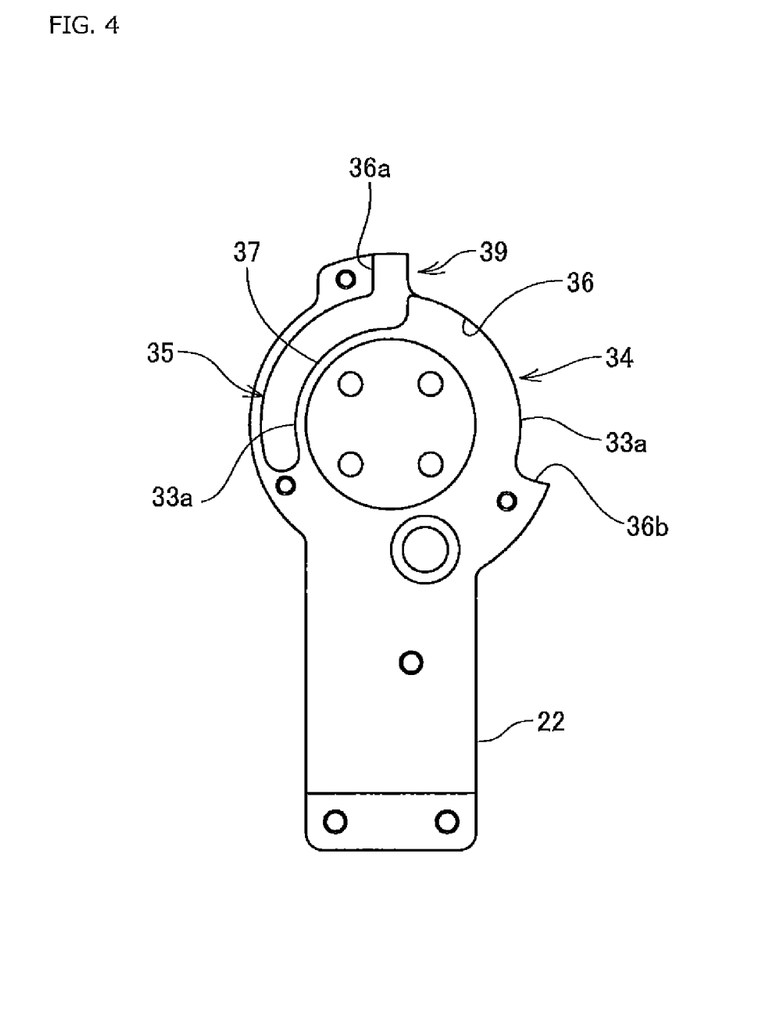
FIG. 4 is a schematic diagram showing an example of guiding paths formed in a second link.

In FIG. 4, the first guiding path 34 includes an outer peripheral groove 36 formed in an outer peripheral edge of the second link 22, and guides the projection 31 along this outer peripheral groove 36 in a clockwise manner. Protruding portions 36a and 36b (an example of the regulating portion of the present application) protruding to the outside are formed in one end and the other end of this outer peripheral groove 36, and movement of the projection 31 is regulated, and the moving range of the projection 31 is specified by this pair of protruding portions 36a and 36b.

In FIG. 4, the second guiding path 35 includes an inner peripheral groove 37 formed inside the outer peripheral edge of the second link 22, and guides the projection 31 along this inner peripheral groove 37 in a counterclockwise manner. One end and the other end of this inner peripheral groove 37 are blocked, and movement of the projection 31 is regulated, and the moving range of the projection 31 is specified by these one end and other end.

Additionally, each of the guiding paths 34 and 35 includes an engagement portion 33a that is formed into an arc-like shape whose radius is the distance between the rotation center of the second link 22 and the projection 31, and that engages with the projection 31, and the projection 31 moves along the engagement portion 33a according to rotation of the second link 22.

Additionally, as shown in FIG. 4, the engagement portion 33a formed in each of the guiding paths 34 and 35 is formed into an arc-like shape having a different radius, and the two guiding paths 34 and 35 communicate with each other via a communication path 39.

The first guiding path 34 and the second guiding path 35 are formed to correspond to the rotation operation of the second link 22 on the basis of the time of the stretching motion of the first link 21 and the second link 22, and are arranged so that the respective ends of the guiding paths 34 and 35 are overlapped on each other in the vertical direction. The communication path 39 is formed to linearly extend in the vertical direction so that these ends communicate with each other, and each of the guiding paths 34 and 35 is provided independently.

Then, it is possible to switch the rotation direction of the second link 22 by moving the projection 31 between the two guiding paths 34 and 35 by using this communication path 39.

Note that the positions of the guiding paths 34 and 35 and the communication path 39 are examples, are not limited, and can be properly arranged and changed on the second link 22. Further, with the changing of the guiding paths 34 and 35 and the communication path 39, the position of the projection 31 and the position of a moving unit 40 described later are also properly changed.

Additionally, the guiding paths 34 and 35 are designed according to the range of movement of a knee joint, and the range of movement (the range of rotation of the second link 22) is specified by the moving range of the projection 31 by these guiding paths 34 and 35.

Additionally, as shown in FIG. 3 and FIG. 5, the joint support unit 20 includes the moving unit 40 that causes the projection 31 to move between the first guiding path 34 and the second guiding path 35, and this moving unit 40 is provided in the first link 21. This moving unit 40 moves the projection 31 to each of the guiding paths 34 and 35 by a link mechanism in the communication path 39.

The moving unit 40 includes the link mechanism constituted by a projection moving member 41 that moves the projection 31, and an operating member 42 that operates the projection moving member 41.

The projection moving member 41 is a linearly extending member, the projection 31 is attached to a tip portion thereof, and the operating member 42 is mutually rotatably coupled to a base end thereof by a connecting pin 43, etc. This projection moving member 41 is arranged in a groove 45 that is formed in the first link 21, and that linearly extends at least in the vertical direction, and moves inside this groove 45 in a predetermined range by operation of the operating member 42.

The operating member 42 is a linearly extending member, a tip portion thereof is provided so as to protrude laterally and to the outside of the first link 21, and to be able to be rotated in a predetermined range, and the projection moving member 41 is mutually rotatably coupled to a base end thereof by the connecting pin 43, etc.

This operating member 42 is provided such that the tip end can be slidably moved between a first position where the projection 31 is maintained on the first guiding path 34, and a second position where the projection 31 is maintained on the second guiding path 35, the projection moving member 41 is moved in the vertical direction via the connecting pin 43 by this sliding operation of the operating member 42, and the projection 31 is moved within the communication path 39.

Figure 5A:
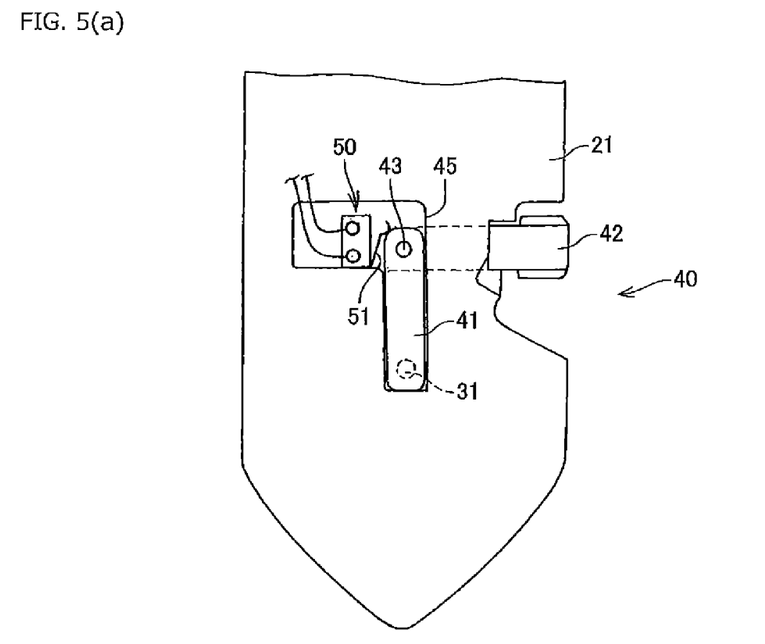
FIG. 5(a) shows a normal rotation position.
Figure 5B:
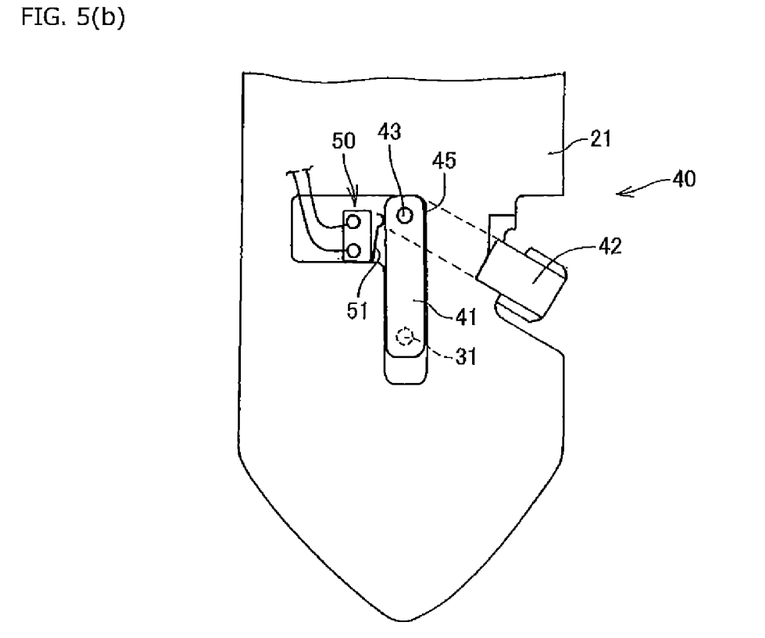
FIG. 5(b) shows a reverse rotation position.

Then, as shown in FIG. 2 and FIG. 5(a), for example, when the operating member 42 is arranged at the second position, and the projection 31 is arranged in a bottom end of the communication path 39, the projection 31 can be moved according to the second guiding path 35, and the second link 22 can be rotated in a counterclockwise manner. On the other hand, as shown in FIG. 5(b), when the operating member 42 is arranged at the first position, the projection moving member 41 is pulled up, and the projection 31 is arranged in a top end of the communication path 39, the projection 31 can be moved according to the first guiding path 34, and the second link 22 can be rotated in a clockwise manner.

In this manner, the moving unit 40 of the present embodiment can move the projection 31 according to the predetermined guiding paths 34 or 35 by switching between the first guiding path 34 and the second guiding path 35 by the sliding operation of the operating member 42, and can switch the operation (rotation) direction of the second link 22.

Additionally this moving unit 40 is provided with an electrical switching unit (an example of a switching device of the present application) that switches the rotation direction by the power source, in the present embodiment, by automatically switching a control program when the operating member 42 is operated.

The electrical switching unit includes a switch 50 that switches the rotation direction by the power source by movement of a contact 51, and the rotation direction of the power source is switched by operation of this switch 50.

This switch 50 is provided to be in the groove 45 formed in the first link 21 and to be adjacent to the projection moving member 41, and is operated between a reverse rotation position (FIG. 5(b)) at which the rotation direction of the power source is reversed by pressing the contact 51 by the projection moving member 41 and moving the contact 51 and a normal rotation position (FIG. 5(a)) at which the rotation direction of the power source is normally rotated without pressing the contact 51 by the projection moving member 41 and without moving the contact 51 with movement of the projection moving member 41 by operation of the operating member 42.

Then, as shown in FIG. 2, when the operating member 42 is operated and the projection 31 is arranged in the second guiding path 35, since the contact is not pressed by the projection moving member 41, and the switch 50 is operated to the normal rotation position, the power source is normally rotated, and rotates the second link 22 in a counterclockwise manner. On the other hand, when the projection 31 is switched to the first guiding path 34, since the contact is pressed by the projection moving member 41, and the switch 50 is operated to the reverse rotation position, the power source is reversely rotated, and rotates the second link 22 in a clockwise manner.

In this manner, the electrical switching unit of the present embodiment can automatically switch the control program (for example, the rotation direction of the power source), according to the switching operation of the guiding paths 34 and 35 by the sliding operation of the operating member 42, is convenient and can easily improve the operativity since electrical switching of the control program can be performed simultaneously with switching of the guiding paths 34 and 35, and can prevent a malfunction that may occur when independently performing a switching operations of a mechanical operation and the electrical control program.

Next, a description will be given of an operation example of the walking support apparatus S of the present embodiment. Note that, in the present embodiment, a description will be given by assuming that in a case where the walking support unit U is worn on a right leg, the second link 22 is rotated in a counterclockwise manner and the second guiding path 35 is used, and in a case where the walking support unit U is worn on a left leg, the second link 22 is rotated in a clockwise manner and the first guiding path 34 is used.

First, using FIG. 6, a description will be given of an operation example in a case where the walking support unit U is worn on the left leg.

After the walking support unit U is worn on the left leg of the user, it is confirmed whether the operating member 42 is arranged at the first position. Here, in a case where the operating member 42 is arranged at the second position, the operating member 42 is moved to the first position by performing sliding operation.

When the operating member 42 is arranged at the first position, the projection 31 is arranged at one end side of the first guiding path 34. Note that, as shown in FIG. 5(*b*), simultaneously with when the operating member 42 is arranged at the first position, the contact 51 is pressed, and the switch 50 is operated to the reverse rotation position.

Figure 6A:
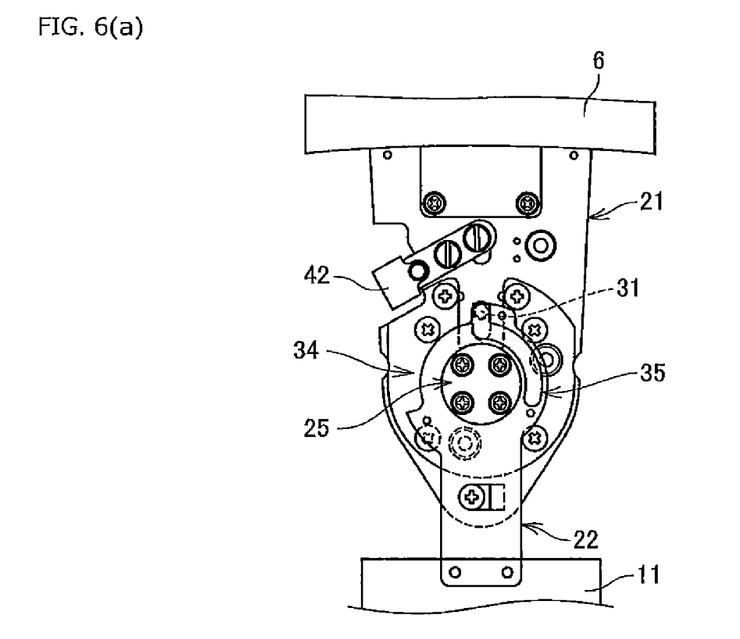
FIG. 6(a) shows a stretched state.
Figure 6B:
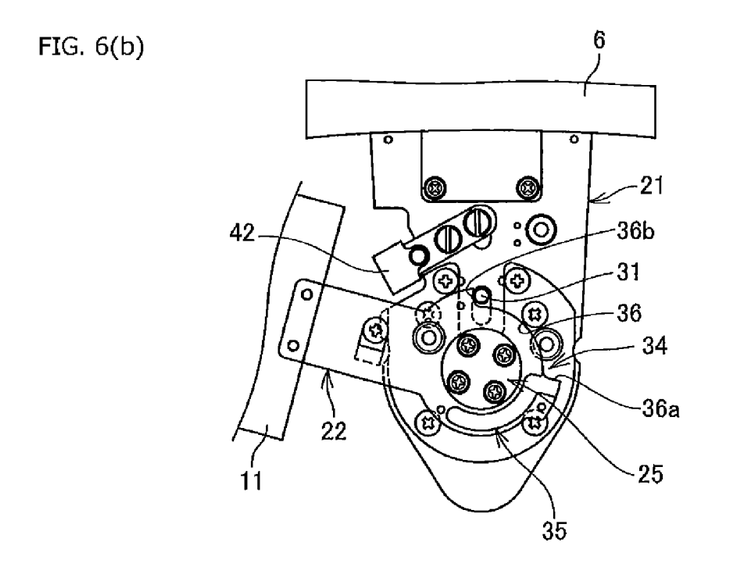
FIG. 6(b) shows a bent state.

Next, when the user perform an ON operation of a power supply, which is not shown, of the walking support unit U, the above-described driving unit is driven. Specifically, the joint support unit 20 drives the second link 22 by performing rotation control of the power source to perform reverse rotation, moves the projection 31 according to the first guiding path 34, and makes the second link 22 oscillate between a stretching motion position shown in FIG. 6(*a*) and a bending motion position shown in FIG. 6(*b*).

Additionally, since the moving range of the projection 31 is regulated by the protruding portions 36*a* and 36*b* in the first guiding path 34, movement of the projection 31 is regulated when the projection 31 reaches the range of movement of a knee joint of the user specified in advance, and thus there is no risk that the second link 22 is driven beyond the predetermined range of movement, and the user can safely use the walking support unit U.

Next, using FIG. 7, a description will be given of an operation example in a case where the walking support unit U is worn on a right leg.

After the walking support unit U is worn on the right leg of the user, it is confirmed whether the operating member 42 is arranged at the second position. Here, in a case where the operating member 42 is arranged at the first position, the operating member 42 is moved to the second position by performing sliding operation.

When the operating member 42 is arranged at the second position, the projection 31 is arranged at one end side of the second guiding path 35. Note that, as shown in FIG. 5(*a*), simultaneously with when the operating member 42 is arranged at the second position, the contact 51 is not pressed, and the switch 50 is operated to the normal rotation position.

Figure 7A:
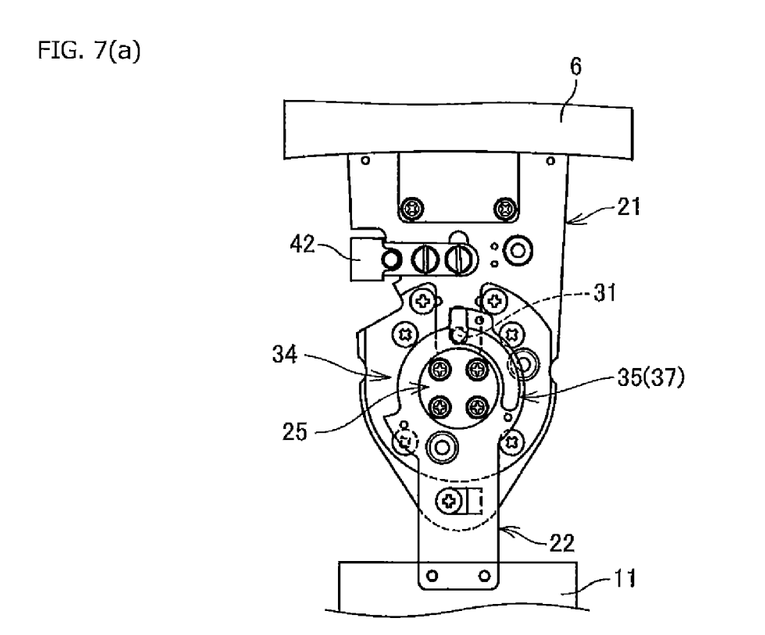
FIG. 7(a) shows a stretched state.
Figure 7B:
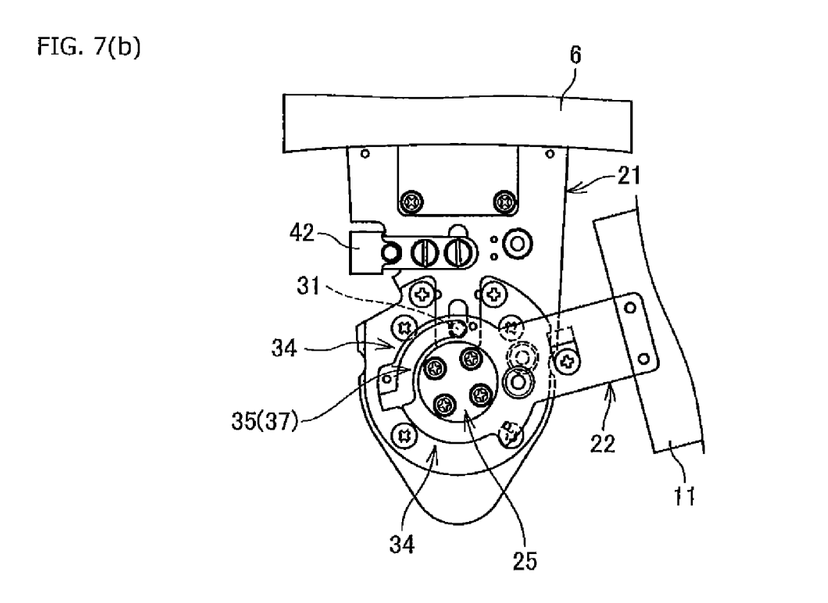
FIG. 7(b) shows a bent state.

Next, when the user perform an ON operation of the power supply, which is not shown, of the walking support unit U, the power source is driven. Specifically, the joint support unit 20 drives the second link 22 by performing rotation control of the power source to perform normal rotation, moves the projection 31 according to the second guiding path 35, and makes the second link 22 oscillate between a stretching motion position shown in FIG. 7(*a*) and a bending motion position shown in FIG. 7(*b*).

Additionally, since the moving range of the projection 31 is regulated by one end and the other end of the inner peripheral groove 37 in the second guiding path 35, movement of the projection is regulated when the projection reaches the range of movement of a knee joint of the user specified in advance, and thus there is no risk that the second link 22 is driven beyond the predetermined range of movement, and the user can safely use the walking support unit U.

Next, using FIG. 1, a description will be given of a wearing example of the walking support apparatus S by the user. Note that, for convenience, a detailed description will be given of an example where the walking support unit U is worn on a right leg.

In the walking support apparatus S of the present embodiment, the waist wearing unit 2 and the walking support unit U can be separated by using the coupling tools 4 and 7, and the walking support apparatus S of the present embodiment is used by wearing the walking support unit U on the upper leg portion 16 and the lower leg portion 17 of the right leg, after the waist wearing unit 2 is worn around the waist of the user.

First, the waist wearing unit 2 is worn around the waist such that the coupling tool 4 is arranged along the lateral surface of the upper leg portion 16 of the user, and the length of the waist belt 3 is adjusted.

Next, the walking support unit U is worn on the right leg. Specifically, the upper leg wearing unit 5 and the lower leg wearing unit 10 are worn on the upper leg portion 16 and the lower leg portion 17 of the user by the attaching tools 8 and 12, and wearing of the walking support apparatus S ends.

Next, as shown in FIG. 7, the operating member 42 is operated, and the projection 31 is arranged in a bottom end portion of the communication path 39. At this moment, the rotation direction of the power source is also controlled to match the rotation direction of the second link 22.

On the other hand, this walking support apparatus S can be used for both left and right, and when worn on a left leg in a manner similar to the above, the operating member 42 may be operated and the projection 31 may be arranged in the top end of the communication path 39, as shown in FIG. 6.

In this manner, since the walking support apparatus S of the present embodiment can automatically switch the control program, and can switch the operation direction of the lower leg wearing unit 10 only by sliding operation of the operating member 42, the walking support apparatus S of the present embodiment is excellent in operativity, and can prevent a malfunction that may occur when independently performing a switching operations of a mechanical operation and the electrical control program. Additionally, since the walking support unit U can be worn on both left and right legs only by reversing the walking support unit U, the cost can be reduced. In addition, since the lower leg wearing unit 10 is not operated beyond the range of movement of a knee joint specified in advance by the rotation regulating unit 30, the walking support apparatus S can be safely used.

Note that the present application is not limited to the present embodiment, and can be implemented in various forms. For example, although the first guiding path 34 is formed in the outer peripheral edge of the second link 22, both of the first and second guiding paths 34 and 35 may be formed inside the second link 22. Additionally, although the moving unit 40 has the link mechanism that uses two members, the moving unit 40 may move the projection 31 by one member, or may be the link mechanism that uses three or more members.

REFERENCE SIGNS LIST

S . . . walking support apparatus, 20 . . . joint support unit, 21 . . . first link, 22 . . . second link, 31 . . . projection, 33 . . . engagement part, 34 . . . first guiding path, 35 . . . second guiding path, 39 . . . communication path, 40 . . . moving unit

The invention claimed is:

1. A joint support unit worn around a joint portion of a user, the joint support unit comprising:
   a first link worn on one end side of the joint portion;
   a second link worn on the other end side of the joint portion, and rotatably coupled to the first link;
   a driving unit configured to perform rotation driving of the second link; and
   a rotation regulating unit configured to regulate a rotation direction and a rotation range of the second link,
   the rotation regulating unit including:
   an engagement body provided in one of the links; and an engagement part provided in the other one of the links, and engaging with the engagement body,
   the engagement part including:
   two guiding paths that guide the engagement body moving according to the rotation direction of the second link in different directions; and a communication path that communicates the two guiding paths to each other, and
   the engagement body being movable between the two guiding paths via the communication path.

2. The joint support unit according to claim 1, wherein each of the guiding paths includes a regulating portion configured to regulate a moving range of the engagement body.

3. The joint support unit according to claim 2, comprising a moving unit configured to move the engagement body to one or the other of the guiding paths.

4. The joint support unit according to claim 3, comprising a switching device configured to mechanically switch a rotation direction of the driving unit, when the engagement body is moved from one of the guiding paths to the other of the guiding paths.

5. The joint support unit according to claim 2, comprising a switching device configured to mechanically switch a rotation direction of the driving unit, when the engagement body is moved from one of the guiding paths to the other of the guiding paths.

6. The joint support unit according to claim 1, comprising a moving unit configured to move the engagement body to one or the other of the guiding paths.

7. The joint support unit according to claim 6, comprising a switching device configured to mechanically switch a rotation direction of the driving unit, when the engagement body is moved from one of the guiding paths to the other of the guiding paths.

8. The joint support unit according to claim 1, comprising a switching device configured to mechanically switch a rotation direction of the driving unit, when the engagement body is moved from one of the guiding paths to the other of the guiding paths.

9. A walking support apparatus comprising:
   an upper leg wearing unit for a knee joint of a leg to an upper leg portion; a lower leg wearing unit for the knee joint to a lower leg portion; and a joint support unit for the knee joint,
   the joint support unit including:
   a first link coupled to the upper leg wearing unit;
   a second link coupled to the lower leg wearing unit, and rotatably coupled to the first link;
   a driving unit configured to perform rotation driving of the second link; and
   a rotation regulating unit configured to regulate a rotation direction and a rotation range of the second link,
   the rotation regulating unit including:
   an engagement body provided in one of the links; and an engagement part provided in the other one of the links, and engaging with the engagement body,
   the engagement part including:
   two guiding paths that guide the engagement body moving according to the rotation direction of the second link in different directions, and a communication path that communicates the two guiding paths to each other, and
   the engagement body being movable between the two guiding paths via the communication path.

* * * * *